(12) United States Patent
Martinez

(10) Patent No.: US 8,302,609 B2
(45) Date of Patent: Nov. 6, 2012

(54) SNORING AND SLEEP APNEA PREVENTION DEVICE

(76) Inventor: Lubin Martinez, Orange, CA (US)

( * ) Notice: Subject to any disclaimer, the term of this patent is extended or adjusted under 35 U.S.C. 154(b) by 112 days.

(21) Appl. No.: 12/889,129

(22) Filed: Sep. 23, 2010

(65) Prior Publication Data

US 2012/0073581 A1 Mar. 29, 2012

(51) Int. Cl.
*A61F 5/56* (2006.01)
*A61C 5/14* (2006.01)
(52) U.S. Cl. ................................... 128/848; 128/860
(58) Field of Classification Search .............. 128/848, 128/859–862; 433/6–7, 140, 148–149, 136, 433/138
See application file for complete search history.

(56) References Cited

U.S. PATENT DOCUMENTS

| 3,132,647 A * | 5/1964 | Corniello ................ 128/848 |
| 5,983,892 A * | 11/1999 | Thornton ............ 128/201.26 |
| 6,766,802 B1 | 7/2004 | Kerpian |
| 6,769,910 B1 | 8/2004 | Patino |
| 7,770,582 B2 * | 8/2010 | Chen et al. ............. 128/848 |
| 2008/0041396 A1 | 2/2008 | Lucker |

* cited by examiner

*Primary Examiner* — Kevin C Sirmons
*Assistant Examiner* — Ophelia Hawthorne
(74) *Attorney, Agent, or Firm* — Lynn & Lynn; John H. Lynn

(57) ABSTRACT

A mouth appliance for maintaining effective airflow in a wearer's airway comprises a frame formed to engage the wearer's upper and lower teeth to retain the frame in a selected position in the wearer's mouth in accord with the wearer's natural bite. A tongue depressor is mounted to the frame and formed to extend to a rear portion of the wearer's throat and exert pressure directly on the tongue in the area of the wearer's soft palate, thereby facilitating comfort and ease in occasional swallowing, while providing airflow effectiveness to prevent the wearer from snoring and experiencing sleep apnea.

2 Claims, 3 Drawing Sheets

SNORING AND SLEEP APNEA PREVENTION DEVICE

BACKGROUND OF THE INVENTION

This invention relates generally to an apparatus and method for prevention a person snoring and having sleep apnea. More particularly, this invention relates to a device that a person places in his mouth to restrain his tongue in such a manner as to prevent it from closing his airway as the person relaxes and falls asleep.

The dangers of snoring and sleep apnea are well-known. There are surgical procedures and various devices that are used to prevent snoring and sleep apnea. None of these prior procedures or devices provides the effectiveness and degree of comfort that many people desire.

SUMMARY OF THE INVENTION

The present invention is an inexpensive orthodontic appliance for preventing the tongue and other tissues of a sleeping person from collapsing into his airway. An appliance according to the present invention comprises a frame formed, and fitted to the wearer's natural bite, to engage the wearer's upper and lower teeth to retain the frame in a selected position in the wearer's mouth. The appliance further comprises a tongue depressor mounted to the frame and formed to extend to a rear portion of the wearer's throat and exert pressure on the tongue in the area of the wearer's soft palate, thereby facilitating comfort and ease in occasional swallowing, while providing airflow effectiveness to prevent the wearer from snoring and experiencing sleep apnea.

The mouth appliance according to the present invention preferably further comprises a pressure adjustment mechanism for adjusting the pressure that the tongue depressor exerts on the wearer's tongue. The pressure adjustment mechanism comprises a pressure adjustment bar that extends between opposing sides of the frame and a pressure adjustment spring having a first end connected to the tongue depressor. A bolt extends from a second end of the spring through a hole in the pressure adjustment bar, and a nut is mounted on the bolt and arranged to adjust the spring tension.

The invention may be better understood and appreciated by referring to the detailed description and to the drawings, which are not to any scale and which show examples of the basic features of the invention.

DETAILED DESCRIPTION OF THE INVENTION

Figure 1:
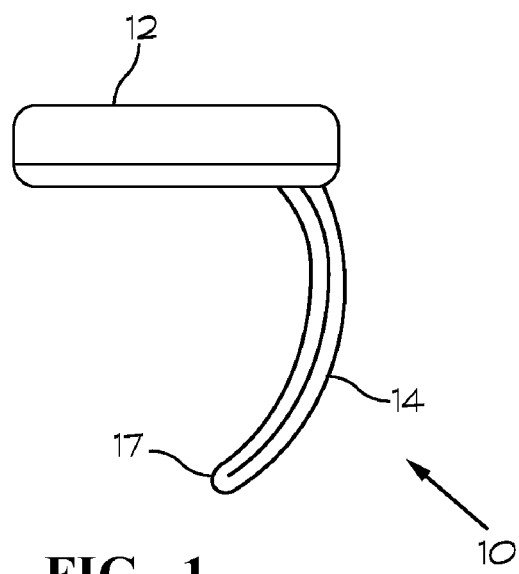
FIG. 1 is a side elevation view of a mouth appliance according to the present invention.
Figure 2:
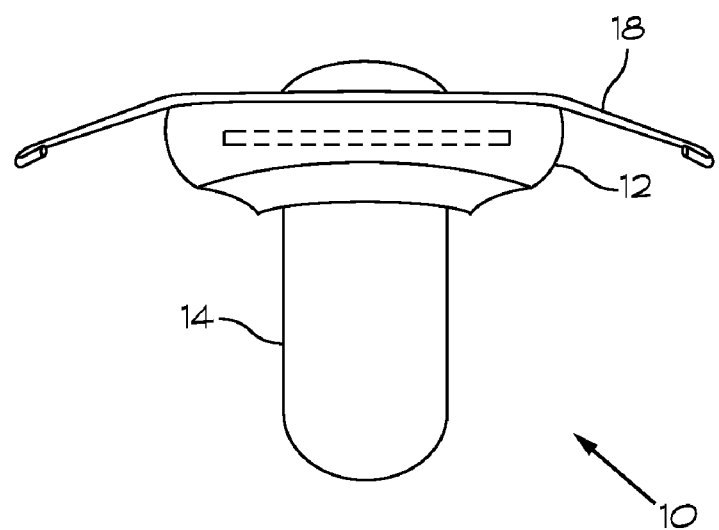
FIG. 2 is a front elevation view of the invention.

Referring to FIGS. 1-6, a mouth appliance 10 according to the present invention includes a frame 12 and a tongue depressor 14 mounted to the frame 12 by means of a pivoting bar 16 and a forward pressure adjustment bar 15. The frame 12 is preferably formed of a hard plastic of a type that is in common orthodontic use. The tongue depressor 14 preferably comprises a hard corrosion resistant metal alloy and preferably includes a smooth-surfaced silicone rubber material or the like at the underside 17 at the point of contact with the tongue.

The frame 12 is configured to engage a wearer's teeth in the manner of a retainer worn by a person undergoing orthodontic treatment. The tongue depressor 14 is formed to extend from the frame 12 into the back of the wearer's mouth.

The mouth appliance 10 according to the present invention allows for the wearer's tongue to rest in a forward position and in as close to a normal position as possible except for pressure being exerted in the area of the soft palate. The tongue depressor 14 is preferably formed to conform to the natural curvature and anatomical characteristics of the wearer's soft palate throat area or pharynx and therefore the natural curvature of the tongue, thereby providing comfort and maximum effectiveness for the airflow in the throat. The mouth appliance 10 also allows and promotes breathing through both the nose and the mouth at night.

Figure 3:
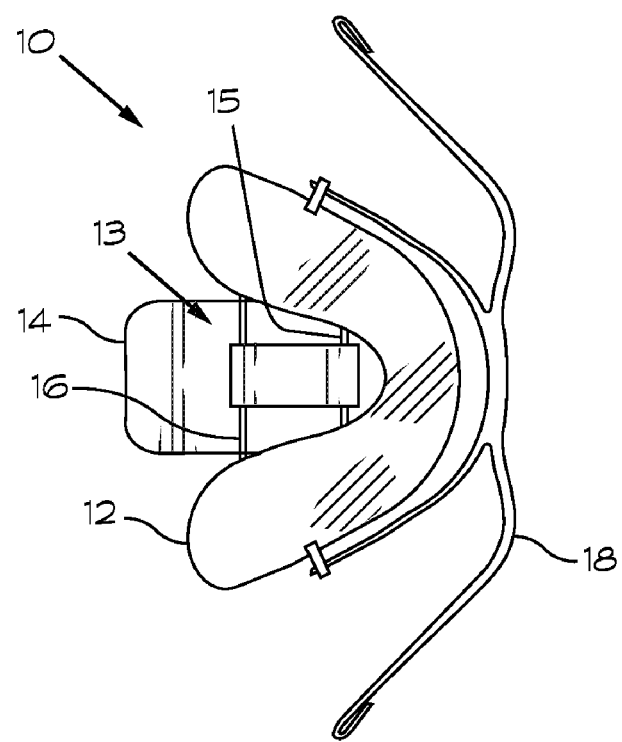
FIG. 3 is a top plan view of the invention.
Figure 4:
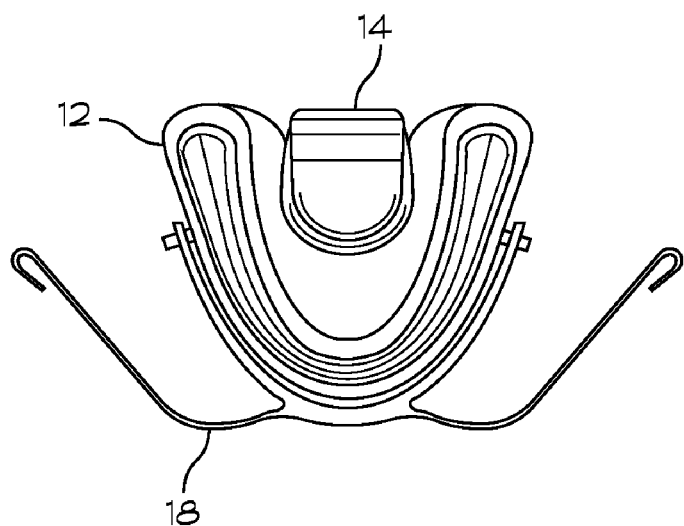
FIG. 4 is a bottom plan view of the invention.

FIG. 3 shows forward pressure adjustment bar 15 that is included in the mouth appliance 10. The forward pressure adjustment bar 15 allows for pressure adjustments at the point where the tongue depressor 14 applies pressure on the tongue, thereby facilitating comfort and ease in occasional swallowing, while providing maximum airflow effectiveness. The tongue depressor 14 is attached to the forward pressure bar 15 by means of a pressure adjustment mechanism 13 that allows for customized pressure settings to maximize comfort and maximum airflow to the wearer. The pivoting bar 16 is situated to the rear of the appliance 10 and is attached to the tongue depressor 14. This allows the tongue depressor 14 to pivot during occasional swallowing at night.

In general the wearing of headgear is not required to use the appliance 10. However, the mouth appliance 10 may also include headgear wires (or tubes) 18 mounted thereto to facilitate the wearing of headgear (not shown) if the wearer wants to use headgear to hold the mouth appliance 10 in a preferred location in his mouth.

Figure 5:
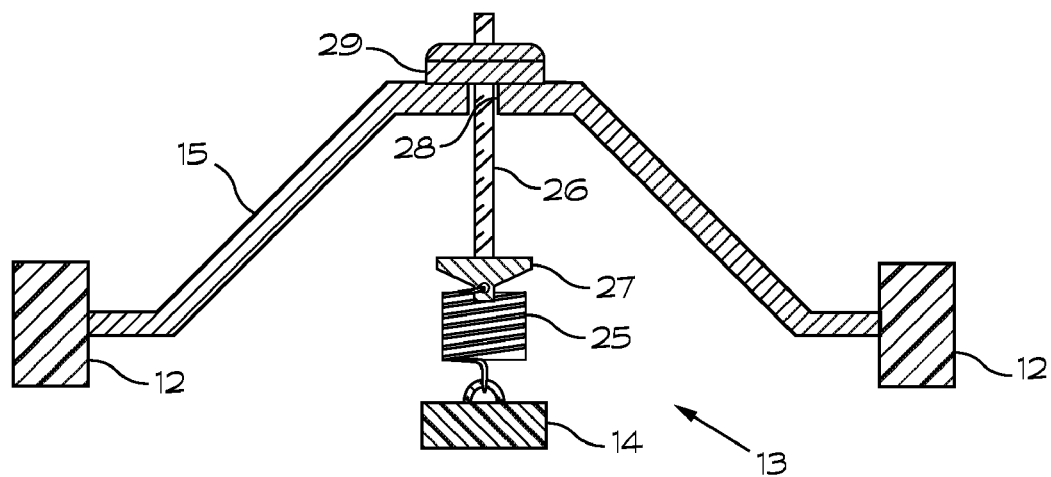
FIG. 5 is a cross sectional view featuring a pressure adjustment mechanism that is included in the invention.
Figure 6:
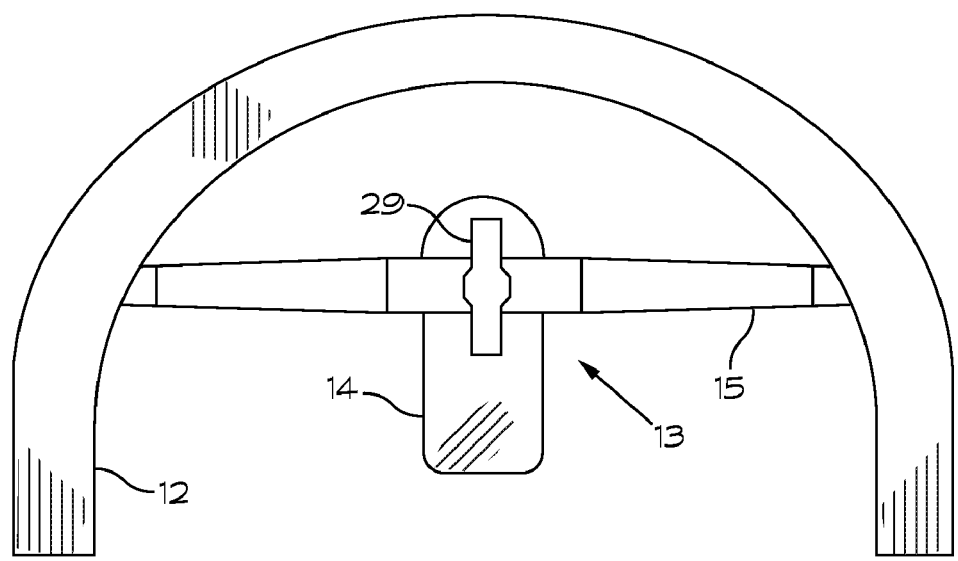
FIG. 6 is a top plan view of the pressure adjustment mechanism of FIG. 5.

FIGS. 5 and 6 show a structure that may be used to form the pressure adjustment mechanism 13. A bolt 26 has a head portion 27 attached to a spring 25 that is also connected to the tong depressor 14. The bolt 26 extends through a hoe 28 in the forward pressure bar 15. A suitable nut 29 may be used to adjust the tension in the spring 25 to control the forward pressure that the tip of the tongue depressor 14 exerts on the wearers' tongue.

Unlike some prior anti-snoring devices, the present invention does not require anything to come in contact with the roof of the wearer's mouth. The roof of a person's mouth typically is a very sensitive area that is easily injured from contact with anything that applies contact and or pressure. The present invention therefore eliminates the potential and almost certain discomfort in the roof of the mouth.

Further, unlike some previous devices, the present invention does not advance the wearer's jaw, which leads to much discomfort at night and into the next day due to the "readjustment" of the jaw joint back to one's own natural bite.

What is claimed is:

1. A mouth appliance for maintaining effective airflow in a user's airway, comprising:
    a frame adapted to engage the user's upper and lower teeth to retain the frame in a selected position in the user's mouth in accord with the user's natural bite;
    a pivoting bar mounted to a rear region of the frame;
    a tongue depressor mounted to the pivoting bar and adapted to extend to a rear portion of the user's throat and exert forward pressure directly on the user's tongue in the area of the user's soft palate, thereby facilitating comfort and ease in occasional swallowing, while providing airflow effectiveness to prevent the wearer from snoring and experiencing sleep apnea; and a forward pressure adjustment bar connected to the tongue depressor and extending between opposite sides of the frame and adapted for adjustment of th forward pressure on the user's tongue to provide maximum comfort and airflow to the user.

2. The mouth appliance of claim 1, further comprises a pressure adjustment mechanism comprising:

a pressure adjustment spring having a first end connected to the tongue depressor;

a bolt extending from a second end of the spring through a hole in the forward pressure adjustment bar; and a nut mounted on the bolt and arranged to adjust the spring tension.

* * * * *